(12) United States Patent
Ahn et al.

(10) Patent No.: US 8,771,949 B2
(45) Date of Patent: Jul. 8, 2014

(54) METHOD OF IDENTIFYING TARGET BIOMOLECULE BY USING PROBE-BINDING FREQUENCY

(75) Inventors: Tae-jin Ahn, Seoul (KR); Su-hyeon Kim, Seoul (KR); Kyoung-gu Woo, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 31 days.

(21) Appl. No.: 13/303,813

(22) Filed: Nov. 23, 2011

(65) Prior Publication Data

US 2012/0220473 A1    Aug. 30, 2012

(30) Foreign Application Priority Data

Feb. 28, 2011  (KR) ........................ 10-2011-0018211

(51) Int. Cl.
*C12Q 1/68*    (2006.01)
(52) U.S. Cl.
USPC ........................................ 435/6.11

(58) Field of Classification Search
None
See application file for complete search history.

(56) References Cited

U.S. PATENT DOCUMENTS

| 7,005,264 | B2 | 2/2006 | Su et al. |
| 2005/0136408 | A1 | 6/2005 | Tom-Moy et al. |
| 2007/0190542 | A1 * | 8/2007 | Ling et al. .......................... 435/6 |
| 2009/0099786 | A1 * | 4/2009 | Oliver et al. .................... 702/19 |

OTHER PUBLICATIONS

Latreille et al., "Optical Mapping as a Routine Tool for Bacterial Genome Sequence Finishing," *BMC Genomics*, 8:321 (2007).
Singer et al., "Nanopore Based Sequence Specific Detection of Duplex DNA for Genomic Profiling," *Nano Letters*, 738-742 (2010).
Nielson et al., "Genotype and SNP calling from next-generation sequencing data," *Nature Reviews*, 12: 443-451 (2011).

* cited by examiner

*Primary Examiner* — Anne Gussow
*Assistant Examiner* — Mindy G Brown
(74) *Attorney, Agent, or Firm* — Leydig, Voit & Mayer, Ltd.

(57) ABSTRACT

An efficient and accurate method of identifying a target biomolecule in a sample by using target molecule-probe binding frequencies is disclosed.

6 Claims, 15 Drawing Sheets

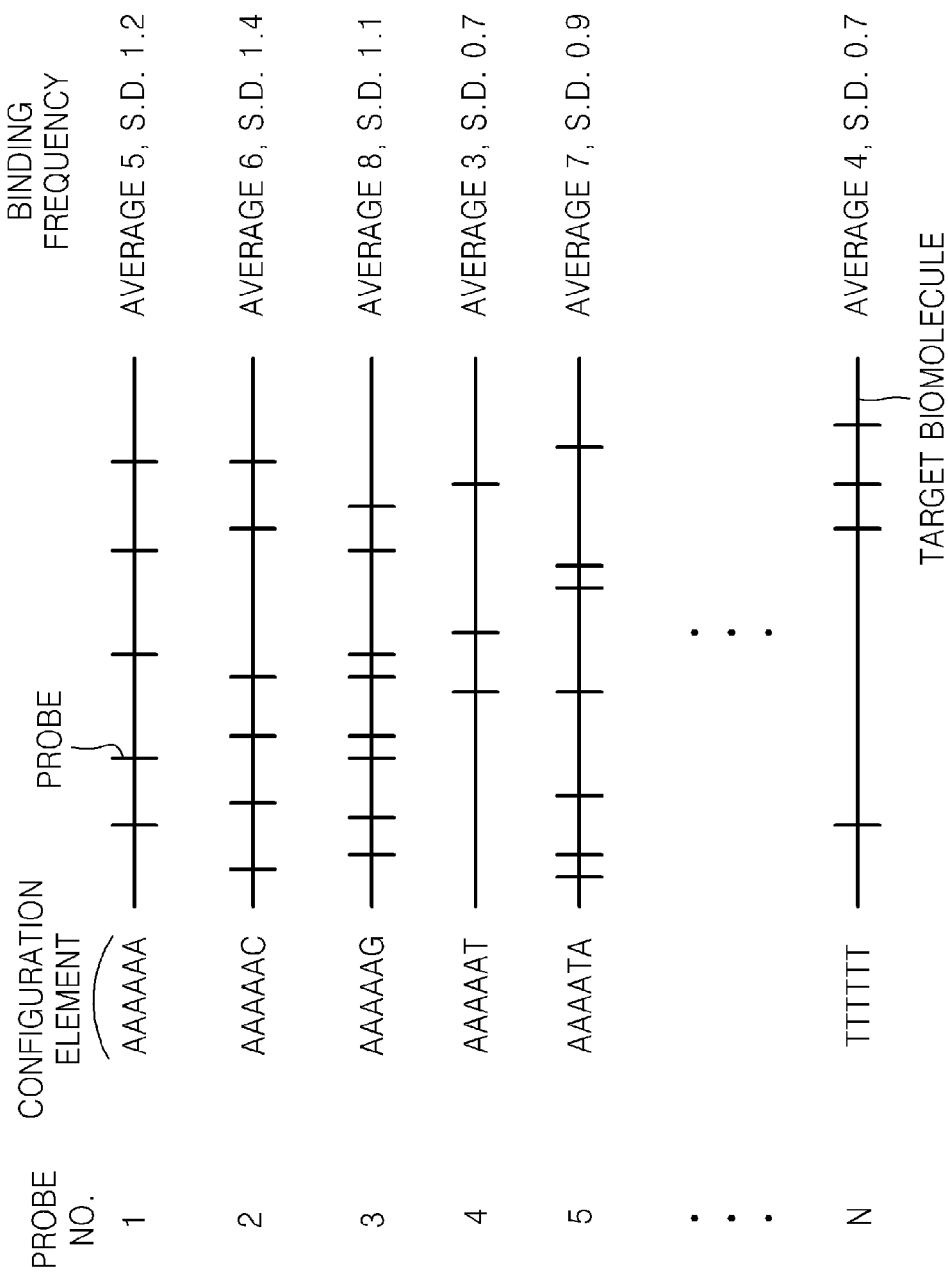

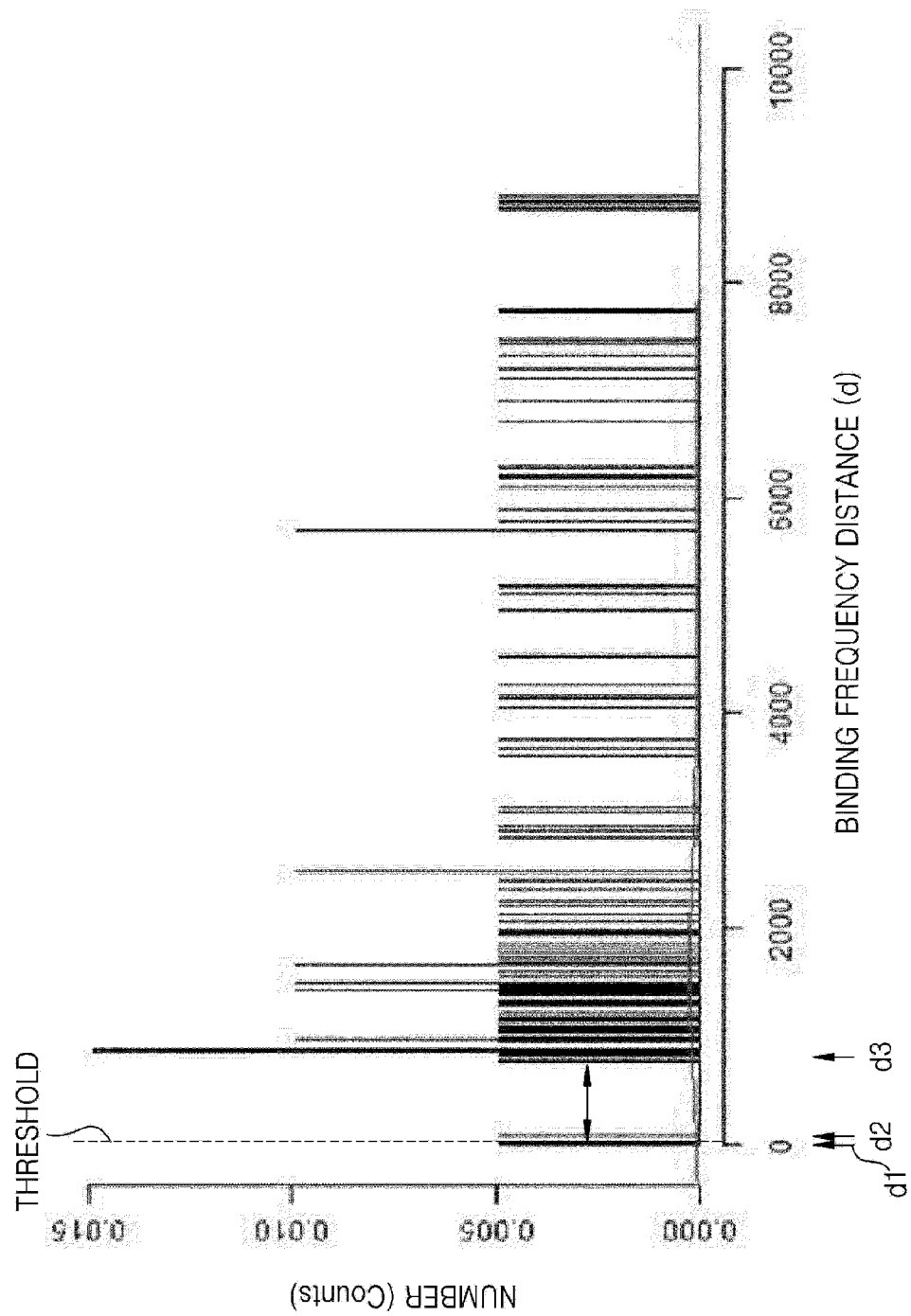

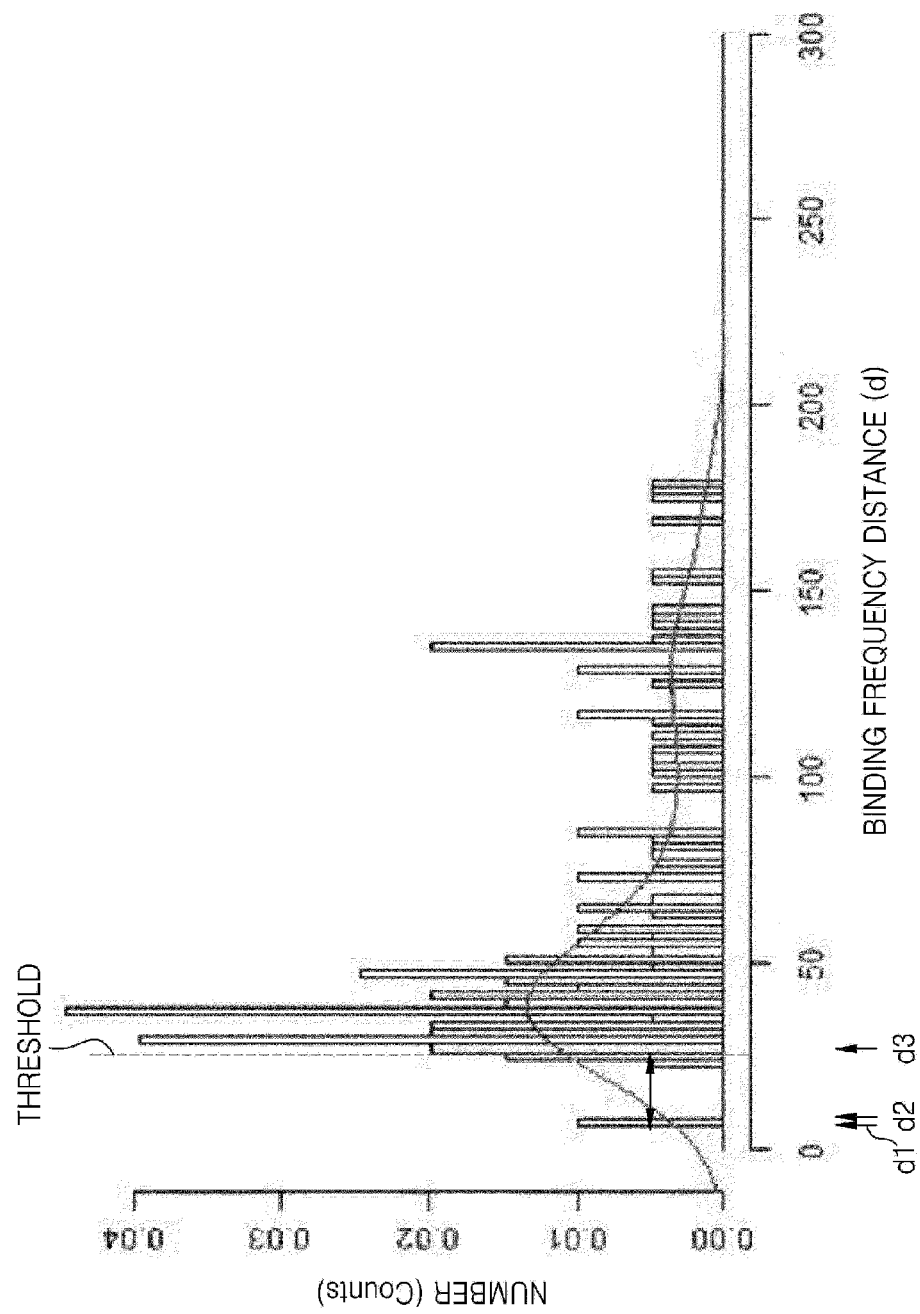

METHOD OF IDENTIFYING TARGET BIOMOLECULE BY USING PROBE-BINDING FREQUENCY

CROSS-REFERENCE TO RELATED APPLICATIONS

This application claims the benefit of Korean Patent Application No. 10-2011-0018211, filed on Feb. 28, 2011, in the Korean Intellectual Property Office, the disclosures of which are incorporated herein by reference.

BACKGROUND

1. Field

The present disclosure relates to a method of identifying a target biomolecule using biomolecular information.

2. Description of the Related Art

Identification of virtually the complete base sequence of the human genome through the Human Genome Project, and various types of ongoing life science research have contributed to building up a great deal of genetic information, which is recently being used in a vast range of fields, including medical diagnosis and treatment, and the environmental and energy fields. In the medical diagnosis and treatment fields, genetic information may be used for various purposes, e.g., to isolate and accurately identify pathogenic bacteria predicted to be a cause of disease, to identify which region of the human genome a gene fragment taken from a patient originates from, and the like. In the environmental and energy fields, genetic information is currently of use in acquiring microorganisms able to biodegrade harmful waste at high efficiency, microorganisms regarded as prospective, high-heat reproductive biological energy sources, and accurately identifying whether they match with a known microorganism. Furthermore, recent advances in information retrieval and processing technologies allow simple access to genetic information by searching online or offline, and performing analysis and processing of the genetic information. For example, a user who has obtained a base sequence of an unknown life form or an unknown biomolecule of interest may identify the target life form or biomolecule of interest by comparison with known genetic information. Existing identification technologies mostly require segmentation of the unknown life form or biomolecule of interest, sequencing the gene fragments, treating with a specific restriction enzyme and performing cleavage pattern analysis, or treating with a specific probe molecule and performing hybridization pattern analysis. These processes are complicated to perform and costly, and take a long processing time. Furthermore, such existing identification technologies are limited when there are variations in genetic sequences or an intrinsic error of the measurement system, and thus are often erroneous, leading to inaccurate identification results.

Therefore, there is a demand for rapid, error-robust identification technologies for identifying a target biomolecule using genetic information.

SUMMARY

Provided are efficient and accurate methods of identifying a target biomolecule in a sample.

Additional aspects of the invention will be set forth in part in the description which follows and, in part, will be apparent from the description, or may be learned by practice of the presented exemplary embodiments.

According to an aspect of the invention, a method of identifying a target biomolecule includes: pbinding each of N probe molecules to a target biomolecule to determine a binding frequency of each probe molecule to the target biomolecule, wherein N≥2 and each probe molecule has a unique configuration element that permits specific binding of the probe molecule to the target molecule; generating a target signature, which is defined by binding frequencies of the individual N probe molecules to the target biomolecule; and identifying the target biomolecule based on a degree of matching between the target signature and a reference signature.

The target biomolecule may include a nucleic acid molecule including a nucleotide, or a peptide molecule including an amino acid.

The identifying of the target biomolecule may include identifying the target biomolecule as being identical to the reference biomolecule if the binding frequencies of the individual probe molecules in the target signature match those in the reference signature within a predetermined confidence level.

The predetermined confidence level may be about 95% or greater with respect to the N probe molecules.

The generating of the target signature may include repeatedly binding each of the N probe molecules to the target biomolecule; and calculating an average binding frequency of each of the N probe molecules with respect to the target biomolecule to generate a target signature, which is defined by the average binding frequencies of the individual N probe molecules.

According to another aspect of the present disclosure, a method of identifying a target biomolecule includes: binding each of N probe molecules to a target biomolecule to generate a target signature, which is defined by the binding frequencies of the individual N probe molecules with respect to the target biomolecule, wherein N≥2 and each probe molecule has a unique configuration element that permits specific binding of the probe molecule to the target molecule; comparing the target signature to a reference signature pool, wherein the reference signature pool includes a reference signature for each of a plurality of reference biomolecules; and identifying the target biomolecule based on degree of matching between the target signature and the reference signatures in the reference signature pool.

The identifying of the target biomolecule may include, if the target signature matches one of the reference signatures in the reference signature pool, identifying the target biomolecule as being identical to the matching reference signature in the reference signature pool.

The identifying of the target biomolecule may include calculating differences between the binding frequencies of the probe molecules in the target signature and the binding frequencies of the corresponding probe molecules in the reference signatures; and identifying the target biomolecule as being identical to the reference biomolecule having one of the reference signatures with a smaller sum of the differences compared to the other reference signatures.

The identifying of the target biomolecule may further include: calculating a binding frequency distance (d) according to Equation (1) below, wherein $x_i$ denotes the $i^{th}$ binding frequency of the target signature, and $y_i$ denotes the $i^{th}$ binding frequency of a reference signature in the reference signature pool; and $$d(\vec{x}, \vec{y}) = \sqrt{\sum_{i=1}^{N} (x_i - y_i)^2} \qquad \text{Equation 1}$$

generating a target-reference distance distribution of binding frequency distance (d) defined by the number of counts with respect to each of the binding frequency distances (d), wherein
the target biomolecule is identified as being identical to one of the reference biomolecules having a binding frequency distance (d) that is smaller than or equal to a threshold in the target-reference distance distribution.

Equation 1 may be replaced with Equation 2 below:

$$d(\vec{x}, \vec{y}) = \frac{\sqrt{\sum_{i=1}^{N} (x_i - y_i)^2}}{N} \qquad \text{Equation 2}$$

If there are at least two binding frequency distances (d) that are smaller than or equal to the threshold in the target-reference distance distribution, the target biomolecule may be determined to be identical to one of the reference biomolecules having the smallest binding frequency distance (d).

The generating of the target signature may include repeatedly binding each of the N probe molecules to the target biomolecule; and calculating an average binding frequency of each of the N probe molecules to the target biomolecule to generate a target signature, which is defined by the average binding frequencies of the individual N probe molecules.

The generating of the target signature may include repeatedly binding each of the N probe molecules to the target biomolecule; and calculating an average binding frequency of each of the N probe molecules to the target biomolecule, thereby generating a target signature, which is defined by the average binding frequencies of the individual N probe molecules. The identifying of the target biomolecule may further include: calculating a binding frequency distance (d) according to Equation (3) below, wherein $x_i$ denotes the $i^{th}$ average binding frequency of the target signature, $y_i$ denotes the $i^{th}$ binding frequency of a reference signature in the reference signature pool, and σi denotes the standard deviation of the $i^{th}$ average binding frequency of the target signature; and $$d(\vec{x}, \vec{y}) = \sqrt{\sum_{i=1}^{N} \frac{(x_i - y_i)^2}{\sigma_i^2}} \qquad \text{Equation 3}$$

generating a target-reference distance distribution of binding frequency distance (d) defined by the number of counts with respect to each of the binding frequency distances (d), wherein the target biomolecule is identified as being identical to one of the reference biomolecules with a binding frequency distance (d) that is smaller or equal to a threshold in the target-reference distance distribution.

Equation 3 may be replaced with Equation 4 below:

$$d(\vec{x}, \vec{y}) = \frac{\sqrt{\sum_{i=1}^{N} \frac{(x_i - y_i)^2}{\sigma_i^2}}}{N} \qquad \text{Equation 4}$$

If there are at least two binding frequency distances (d) that are smaller than or equal to the threshold in the target-reference distance distribution, the target biomolecule may be determined to be identical to one of the reference biomolecules having the smallest binding frequency distance (d).

BRIEF DESCRIPTION OF THE DRAWINGS

These and/or other aspects of the invention will become apparent and more readily appreciated from the following description of exemplary embodiments, taken in conjunction with the accompanying drawings of which:

FIG. 7 is a schematic diagram illustrating a target biomolecule identification method according to another embodiment, which includes repeatedly binding N different probe molecules to a target biomolecule to obtain an average binding frequency and standard deviation for each different probe molecule to generate a target signature;

FIGS. 9A, 9B, and 9C each present a target-reference distance distribution of binding frequency distance (d), in which a possible location error of 0 nucleotides (FIG. 9A), +10 nucleotides (FIG. 9B), or +50 nucleotides (FIG. 9C) for the measuring equipment is reflected in generating the target-reference distance distribution.

DETAILED DESCRIPTION

Figure 1:
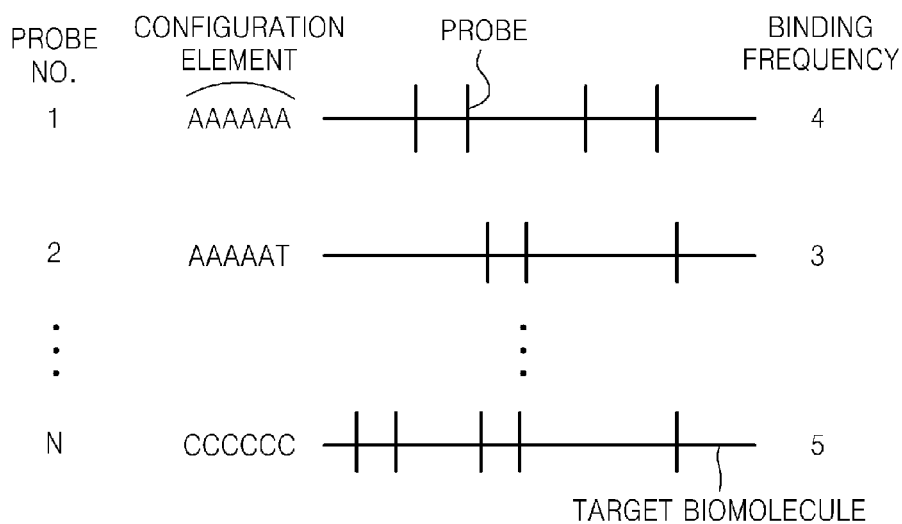
FIG. 1 is a schematic diagram illustrating binding N different probe molecules, having the configuration elements shown on the left, to a target biomolecule to generate a target signature.

Reference will now be made in detail to exemplary embodiments, examples of which are illustrated in the accompanying drawings, wherein like reference numerals refer to like elements throughout. In this regard, the exemplary embodiments may have different forms and should not be construed as being limited to the descriptions set forth herein. Accordingly, the embodiments are merely described below, by referring to the figures, to explain aspects of the invention.

FIG. 1 illustrates a process of binding N different probe molecules to a target biomolecule to generate a target signature. The process illustrated in FIG. 1 involves providing N probe molecules able to bind to a target biomolecule and having different configuration elements; wherein N is the number of probe molecules and N≥2. Binding each of the N probe molecules individually to the target biomolecule to determine the binding frequency of each probe to the target biomolecule generates a target signature, defined by the binding frequencies of the individual N probe molecules to the target biomolecule.

In an embodiment, the method of identifying a target biomolecule may include providing N probe molecules able to bind to the target biomolecule and having different configuration elements, wherein N≥2.

The target biomolecule, which can be an unidentified biomolecule taken from an individual, may be any type of biomolecule. The target biomolecule may be, but is not limited to, a nucleic acid molecule, or a peptide molecule. The target biomolecule may be present in a sample taken from an individual, for example, a liquid sample. The target biomolecule may include a subunit. In some embodiments, if the target molecule is a nucleic acid molecule, the subunit may be a nucleotide, or if the target molecule is a peptide molecule, the subunit may be an amino acid. A target biomolecule may be prepared to have a given length if required. In some embodiments, if the target molecule s a nucleic acid molecule, it may include subunits such that the nucleic acid molecule is about 100 kbp in length.

A probe molecule may include configuration elements capable of binding to a target molecule. The configuration elements may include any material capable of binding to the subunits of the target molecule. In some embodiments, if the target biomolecule is a nucleic acid molecule, the configuration elements may include nucleotides capable of complementary binding to a certain nucleotide sequence of the target nucleic acid molecule. If the target molecule is a peptide molecule, the configuration elements may include one or more amino acids capable of complementary binding to part of the amino acid sequence of the target peptide molecule. The probe molecules may be constructed by a user if required, and in another embodiment, may be selected from among known probe molecules, e.g., a commercially available probe, provided along with information on the binding specificity of the probe. Any appropriate kind of probe molecule may be used as long as it includes configuration elements able to bind to the target biomolecule. In some embodiments the probe molecules may be selected by known dimensional reduction or feature selection. The probe molecules may be prepared to have a given length. In some embodiments, if a probe molecule comprises an oligonucleotide, it may be about 5 bases to about 100 bases in length. The N probe molecules, each including different configuration elements, may be used as described above. The maximum number of probe molecules is not particularly limited as long as there are at least two.

In an embodiment, the method of identifying the target biomolecule may include binding each of the N probe molecules to the target biomolecule to determine a binding frequency of the ith probe molecule to the target biomolecule, where i is an integer from 1 to N, in order to generate a target signature, which is defined by the binding frequencies of the individual N probe molecules to the target biomolecule.

Referring to FIG. 1, the N probe molecules are bound to the target biomolecule, and binding frequencies of the individual N probe molecules are counted. The N probe molecules may have different binding frequencies. The N probe molecules may include different configuration elements, while the target biomolecule may include various subunits able to bind to the configuration elements. This may lead to the varying binding frequencies of the individual N probe molecules to the target biomolecules. In the embodiment shown in FIG. 1, the N probe molecules have different nucleotide base sequences as their configuration elements, that is, the first probe molecule has the base sequence AAAAAA as its configuration element, the second probe molecule has the base sequence AAAAAT as its configuration element, and the $N^{th}$ probe molecule has the base sequence CCCCCC as its configuration element. The N probe molecules are sequentially permitted to bind to the target biomolecule, and probes 1, 2, and N shown in FIG. 1 are found to have binding frequencies of 4, 3, and 5, respectively. A target signature defined by the binding frequencies of the N binding frequencies may be generated. Since the target signature consists of the different binding frequencies of the N different probe molecules to the target biomolecule, it is equivalent to the target biomolecule and may be of use as a tool to qualify and identify the target biomolecule by comparison to a reference signature, which will be described below. The target signature is a tool to qualify the target biomolecule. For example, when the N probe molecules are bound to at least two different target biomolecules including different subunits, the N probe molecules may show different binding frequencies to the different target biomolecules, thus allowing generation of unique target signatures characterizing each of the at least two target biomolecules.

Figure 6:
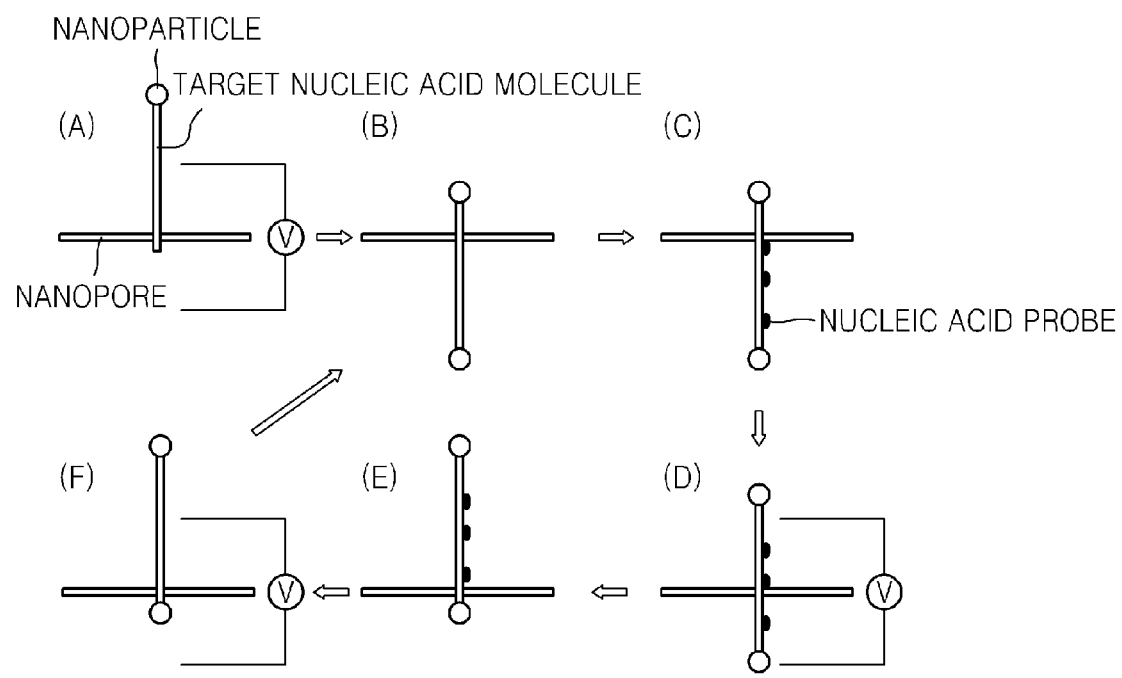
FIG. 6 is a schematic diagram illustrates a process of measuring the binding frequency of a probe molecule to a target binding molecule, using nanoparticles and nanopores.

There are various methods to measure the binding frequencies of probe molecules to a target molecule by binding the probe molecules thereto. For example, as illustrated in FIG. 6, the binding frequency may be measured using a nanopore detector including nanoparticles and nanopores that are able to bind to the target biomolecule. For example, when the target biomolecule includes single-stranded target nucleic acid molecules, and the probe molecules include single-stranded nucleic acid probes, the binding frequencies may be measured using a nanopore detector and nanoparticles, wherein the nanopore detector may include an operably disposed signal detection unit and nanopores having a size large enough to allow passage of the target nucleic acid molecules and/or bound complexes of the target nucleic acid molecules and the nucleic acid probes. The nanoparticles may be able to specifically bind to opposite termini of the target nucleic acid molecules and have a size larger than the nanopores such that the nanoparticles cannot pass through the nanopores. The nanopore detector may include a first chamber disposed in a direction with respect to the nanopores, and a second chamber disposed in a direction with respect to the nanopores opposite to the first chamber. Voltages having opposite polarities may be applied to the first and second chambers. Referring to FIG. 6, after the target nucleic acid molecule with a nanoparticle bound to one of its ends is placed in the first chamber of the nanopore detector, opposite voltages may be applied to the first and second chambers. In one embodiment, a negative voltage may be applied to the first chamber, while a positive voltage is applied to the second chamber (Step A). In this embodiment, the target nucleic acid molecule is negatively charged, and begins migrating from the first chamber to the second chamber through a nanopore of the nanopore detector, due to an electric repelling force of the first chamber and an electric pulling force from the second chamber. Then, a nanoparticle is bound to the other end of the target nucleic acid molecule in the second chamber (Step B). Due to having a nanoparticle bound to each end of the target nucleic acid molecule, the target nucleic acid molecule may not completely pass through the nanopore. Subsequently, molecules of a first probe are bound to the target nucleic acid molecule in the second chamber of the nanopore detector (Step C). Voltages are applied to the first and second chambers of the nanopore detector to migrate the target nucleic acid molecule with the first probe molecules bound thereto from the second chamber to the first chamber. At the same time, the number of first probe molecules bound to the target nucleic acid molecule is counted (Step D). The signal detection unit, which is operably disposed to detect signals from the nanopores, detects a change in signal generated when target nucleic acid molecules bound with the first probe molecules move through the nanopores. These signals may include physical or electrical signals that are generated or varied when the target nucleic acid molecule or the target nucleic acid molecule bound with the first probe molecules pass through the nanopores. In some embodiments, the signals may include, but are not limited to, an optical signal, an ion blockage current, a capacity, a voltage, a current, and the like. Once the target nucleic acid molecule bound with the first probe molecules has, been completely moved to the first chamber as far as permitted by the bound nanoparticle in the second chamber, counting the number of bound first probe molecules is terminated (Step E). Subsequently, first probe molecules are removed from the target nucleic acid molecule (Step F). The removing of the first probe molecules may be performed by various methods, for example, by adjusting a temperature or pH of the sample or by treatment with a buffer or a washing solution. Next, the above-described steps B to F are repeated using molecules of a second probe. In this way, the binding frequencies of the N probe molecules to the target biomolecule may be measured.

Figure 2:
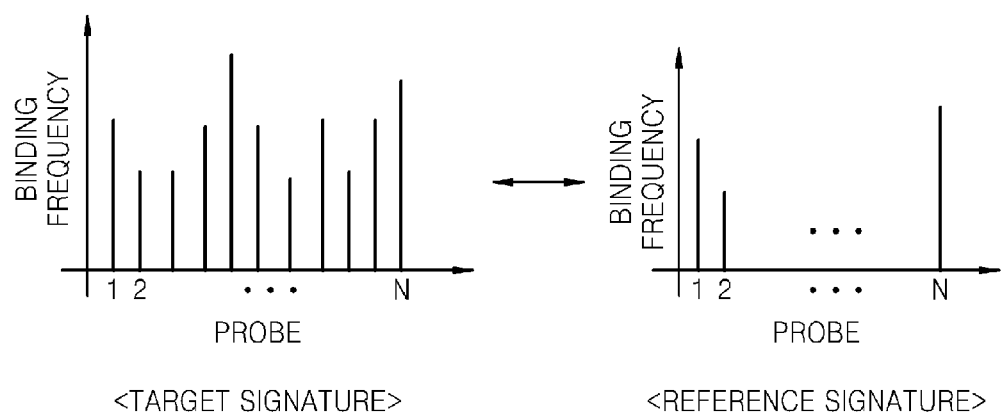
FIG. 2 is a schematic diagram illustrating the process of comparing the target signature generated in the process of FIG. 1 with a reference signature of a known reference biomolecule.

FIG. 2 illustrates a process of comparing the target signature generated in the process of FIG. 1 with a reference signature of a known reference biomolecule. A reference signature is defined by the binding frequencies of the individual N probe molecules to a reference biomolecule, which is of the same type as the target biomolecule. The reference signature shown in FIG. 2 was generated by binding the N probe molecules to the known reference biomolecule to obtain the binding frequencies of the individual N probe molecules to the reference biomolecule. In FIG. 2, identifying the target biomolecule is based on the degree of matching between the target signature and the reference signature.

According to an embodiment, the method of identifying the target biomolecule may include binding each of the N probe molecules to a known reference biomolecule, which is of the same kind as the target biomolecule, to generate a reference signature, defined by the binding frequencies of the individual N probe molecules to the reference biomolecule.

A reference biomolecule is a biomolecule to be compared with a target biomolecule, which is of the same type as, but distinguished from, the target biomolecule, and about which information is widely known. For example, if the target biomolecule includes a nucleic acid molecule, the reference biomolecule also includes a nucleic acid molecule, information about which, including its nucleotide base sequence information, is known. If the target molecule includes a peptide molecule, the reference biomolecule also includes a peptide molecule, information about which, including its amino acid sequence information, is known. Information about the reference biomolecule may be retrieved online or offline from a database server of a commercial or noncommercial entity, and may be processed using various data analysis tools. In some embodiments the database server may be the genome database available from the United States National Institutes of Health (NIH) National Center for Biotechnology Information (NCBI) and the data analysis tools may include BLAST, available, for example via the Internet from NCBI. Therefore, the reference signature may be generated computationally based on information about the N probe molecules and the information about the reference biomolecule, by using a data analysis tool, such as BLAST. For example, base sequence information about the N nucleic acid probe molecules may be aligned against the base sequence information of a reference nucleic acid sequence, and based on the complementary hits determined for each probe, thereby permitting calculation of probable frequencies of complementary binding of the nucleic acid probe molecules to the reference nucleic acid molecule. A reference signature defined by the binding frequencies of the N probe molecules may then be generated. Since the reference signature consists of the different binding frequencies of the N different probe molecules, it may be used as a tool to qualify and identify the reference molecule and to identify the target biomolecule by comparison, as described above. The reference signature is a tool to characterize the reference biomolecule. For example, when the N probe molecules are processed to bind to at least two different reference biomolecules including different subunits, the N probe molecules may show different binding frequencies with respect to the different reference biomolecules, thus allowing generation of different reference signatures to characterize each of the at least two different reference biomolecules. An example of a reference signature generated as described above is illustrated in FIG. 2 (on the right).

In an embodiment of the present disclosure, the method of identifying the target biomolecule may include identifying the target biomolecule based on the degree of matching between the target signature and a reference signature.

Referring to FIG. 2, a process of comparing the target signature (on the left) and the reference signature (on the right) is illustrated. Whether or not the target biomolecule having the target signature is identical to the reference biomolecule having the reference signature may be identified based on the degree of matching between the target signature and the reference signature. If the target signature completely matches the reference signature, i.e., if the binding frequency of every probe molecule in the target signature matches that of the corresponding probe molecule in the reference signature, the target biomolecule may be determined or identified to be identical to the reference biomolecule. Even if the target signature does not completely match the reference signature, if the binding frequencies of the individual probe molecules in the target signature match those of the probe molecules in the reference signature at a predetermined confidence level, i.e., within a statistically reliable range, the target biomolecule may be determined or identified as being identical to the reference biomolecule. The predetermined confidence level may vary according to characteristics of the target biomolecule and reference biomolecules, environmental conditions, information quantity, and the like. The predetermined confidence level may be about 95% or greater with respect to the N probe molecules, and in some embodiments, may be about 99% or greater. For example, when one hundred probe molecules including different configuration elements are used to generate a target signature and a reference signature that include the binding frequencies of the probe molecules to the target and reference biomolecules, respectively, if the degree of matching between the binding frequencies of the corresponding probe molecules of the target signature and the reference signature, as a result of comparison, is greater than or equal to a predetermined confidence level, for example, 95% or greater, or 99% or greater of the total number of the 100 probe molecules, the target biomolecules may be determined or identified as being identical to the reference biomolecule.

Figure 3:
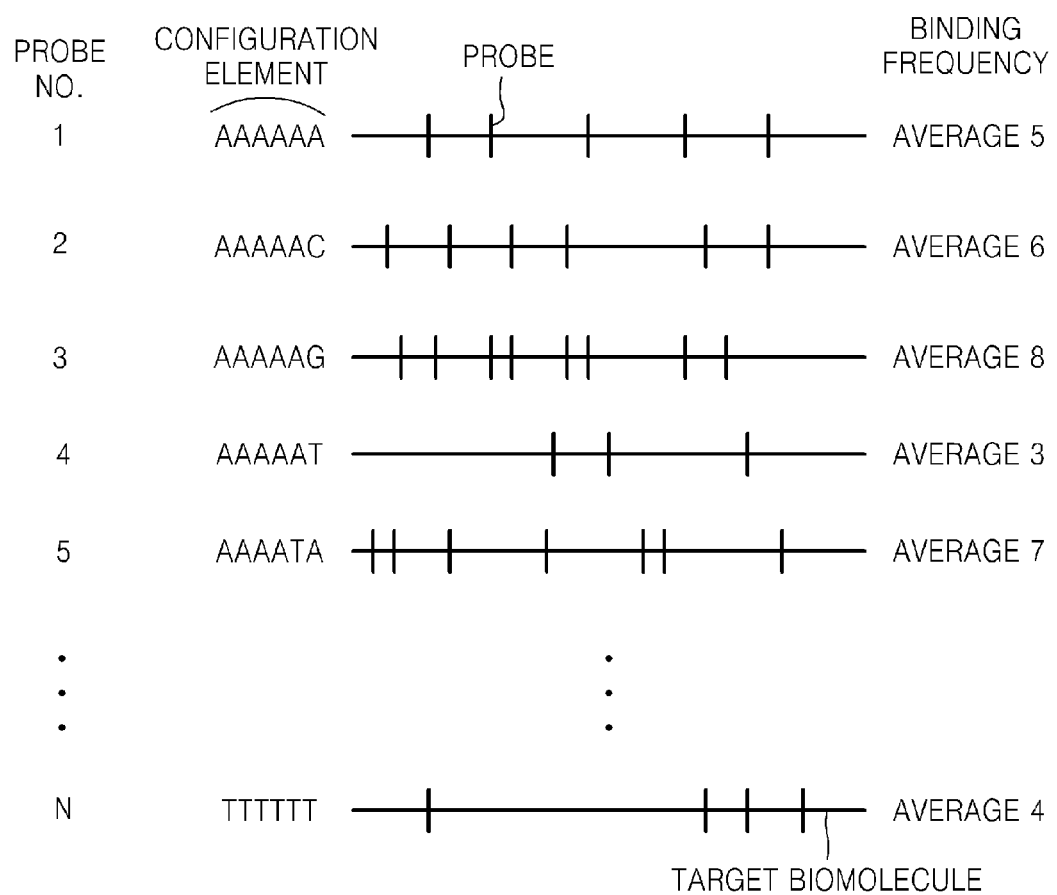
FIG. 3 is a schematic diagram illustrating a process of binding N different probe molecules to a target biomolecule to generate a target signature using the average binding frequencies of the individual probe molecules to the target biomolecule, obtained in replicate binding experiments for each probe.

FIG. 3 illustrates a process of generating a target signature in which binding of each of N different probe molecules to a target biomolecule is performed in replicate to generate average binding frequencies of the individual N probe molecules to the target biomolecule.

In an embodiment of the target biomolecule identification method, generating the target signature may include repeatedly binding each of the N probe molecules to the target biomolecule and calculating an average binding frequency of each of the N probe molecules to the target biomolecule, thereby generating a target signature, which is defined by the average binding frequencies with the individual N probe molecules.

In generating the target signature, to measure the binding frequency of each of the N probe molecules, the N probe molecules may be each bound only one time to the target biomolecule. In some embodiments, the N probe molecules may be each bound to the target biomolecule in at least two experiments. The probe molecules may include configuration elements able to bind to the target biomolecule. However, it may be difficult to determine whether the results of binding the probe molecules to the target biomolecule are accurate, depending on the kind and/or characteristics of the target biomolecule, environmental conditions of the binding experiment, or an error in measurement equipment used in the binding experiment. For example, even if a nucleic acid probe includes configuration elements complementary to a target nucleic acid molecule, the nucleic acid probe may not bind to the target nucleic acid molecule. On the other hand, if a nucleic acid probe includes configuration elements that are non-complementary to the target nucleic acid molecule, the nucleic acid probe may bind to the target nucleic acid molecule. Therefore, to ensure reliability of the measured binding frequencies of the N probe molecules, at least two experiments for determining binding of each of the N probe molecules to the target biomolecule may be performed to calculate average binding frequencies of the individual N probe molecules, thereby generating a target signature, which is defined by the average binding frequencies of the N probe molecules. The repeated binding experiments may be performed at least as many times as necessary to attain statistically reliable binding frequency results. Referring to FIG. 3, a first probe molecule (configuration element: AAAAAA), a second probe molecule (configuration element: AAAAAC), a third probe molecule (configuration element: AAAAAG), a fourth probe molecule (configuration element: AAAAAT), a fifth probe molecule (configuration element: AAAATA), and an $N^{th}$ probe molecule (configuration element: TTTTTT) may be each subjected to at least two experiments to determine binding to the target nucleic acid molecule, and an average binding frequency of each of the probe molecules to the target biomolecule may be calculated. For the example shown in FIG. 3, the average binding frequencies of the first to $N^{th}$ probe molecules are 5, 6, 8, 3, 7, and 4, respectively. In this embodiment, the target signature of the target nucleic acid molecule is defined with the average binding frequencies of the N probe molecules to the target nucleic acid molecule.

Figure 4:
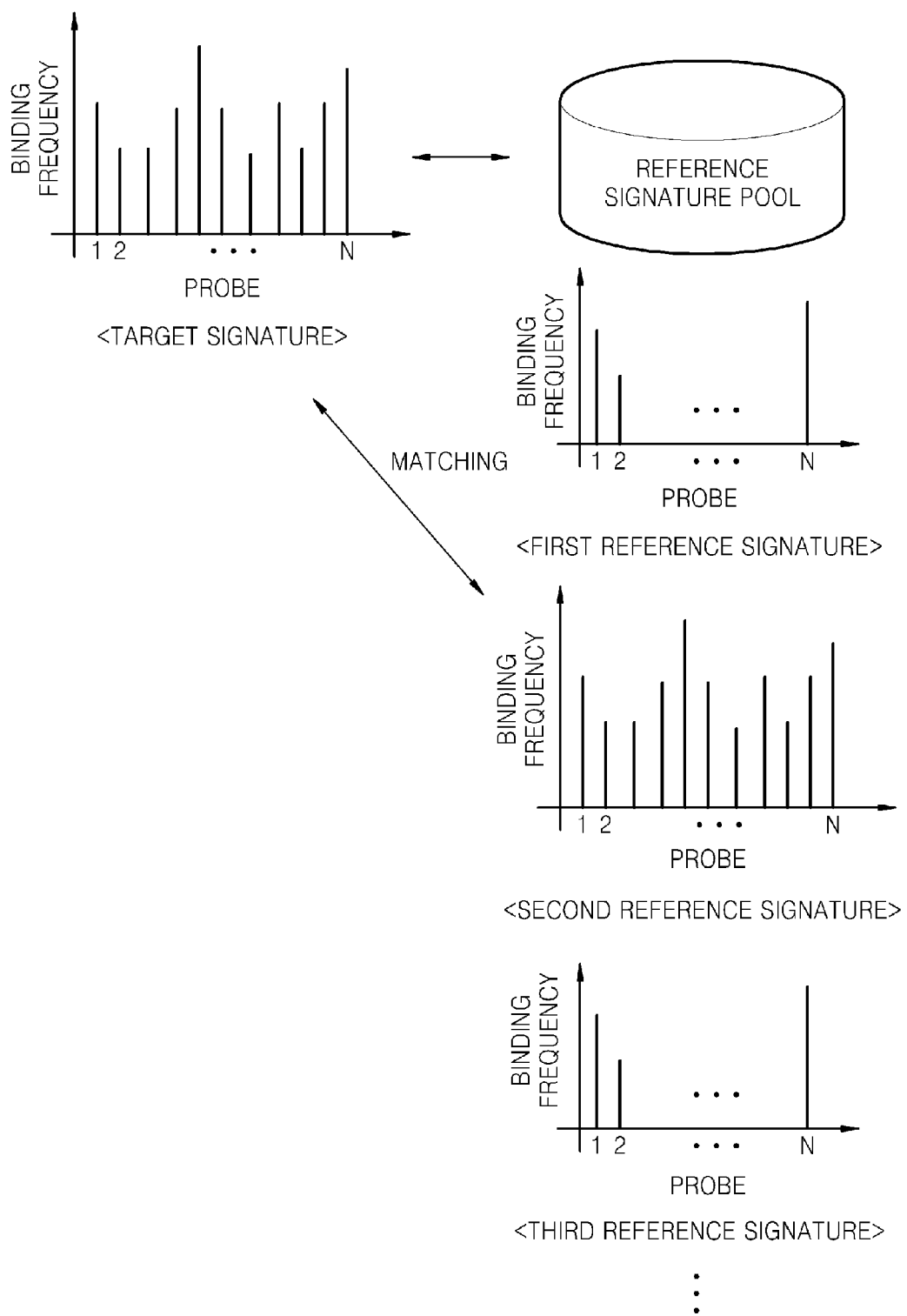
FIG. 4 is a schematic diagram illustrating the process of comparing a target signature for the N probes generated in the process of FIG. 1 or 3 with a reference signature pool including reference signatures for the N probes generated for at least two different known reference biomolecules.

FIG. 4 illustrates a process of comparing a target signature generated in the process of FIG. 1 or 3 with a reference signature pool including at least two reference signatures characterizing at least two different known reference biomolecules.

In another embodiment of the present disclosure, the method of identifying the target biomolecule may include: providing N probe molecules able to bind to the target biomolecule and having different configuration elements, wherein N is an integer greater than or equal to two; binding each of the N probe molecules to the target biomolecule to generate a target signature, which is defined by the binding frequencies of the individual N probe molecules with respect to the target biomolecule; and identifying the target biomolecule based on degrees of matching between the target signature and reference signatures in a reference signature pool. In some embodiments, the method further includes generating a reference signature pool. In an embodiment, generating a reference signature pool comprises binding each of the N probe molecules to at least two different known reference biomolecules to determine a reference signature for each of the reference biomolecules, wherein a reference signature is defined by the binding frequencies of the individual N probe molecules to the corresponding reference biomolecule. In another embodiment, generating a reference signature pool comprises computing a binding frequency for each of the N probe molecules to at least two different known reference biomolecules to determine a reference signature of binding frequencies of the individual N probe molecules to the corresponding reference biomolecule for each of the reference biomolecules.

Referring to FIG. 4, the target signature (on the left), and the reference signature pool (on the right) including first to third reference signatures are illustrated. Details of the target signature and the reference signatures have been described above.

The reference signature pool may include at least two reference signatures, which are defined by the binding frequencies of the individual N probe molecules with respect to at least two different known reference biomolecules that are of the same kind as the target biomolecule. A method of generating the reference signatures of the reference signature pool is as described above. In an embodiment of the present disclosure, the method of identifying the target biomolecule may include identifying the target biomolecule based on degrees of matching between the target signature and reference signatures of the reference signature pool. If the target signature is identical to one of the reference signatures of the reference signature pool, the target biomolecule may be determined or identified as being identical to the reference biomolecule having the identical reference signature of the reference signature pool. Regarding the degree of matching between the target signature and the reference signatures of the reference signature pool necessary for accurate identification of a target biomolecule, if the binding frequencies of the N probe molecules in the target signature match with those in the reference signatures of the reference signature pool at a predetermined confidence level, for example, at about 95% or about 99% or greater of the total number N, the target biomolecule may be determined or identified as being identical to the reference biomolecule having the matching reference signature. Generating the target signature may include repeatedly binding each of the N probe molecules to the target biomolecule and calculating an average binding frequency of each of the N probe molecules with respect to the target biomolecule, which defines a target signature. Identifying the target biomolecule based on the target signature may include calculating, for each of the N probes, the difference between the binding frequency of the probe molecule in the target signature and the binding frequency of the corresponding probe molecule in the at least two reference signatures; and identifying the target biomolecule as being identical to the reference molecule having the reference signature with the smaller sum of the differences in the N binding frequencies compared to the other reference signatures. For example, differences between the binding frequencies of the N probe molecules in the target signature and the binding frequencies of the N probe molecules in each of the reference signatures of a reference signature pool are calculated to find the target signature-reference signature combination having the smallest difference. The target biomolecule may then be determined or identified as being identical to the reference biomolecule of the target signature-reference signature combination having the smallest difference. Referring to FIG. 4, the binding frequencies of the N probe molecules in the target signature appear to match with the binding frequencies of the N probe molecules in the second reference signature, and thus the target biomolecule may be determined or identified as being identical to a second reference biomolecule having the second reference signature. The reference signature pool may be generated at any time so long as it is after provision of the N probe molecules, and in some embodiments, may be generated before or after generation of the target signature of the target biomolecule. The reference signature pool may be generated by experiment or computationally.

Figure 5:
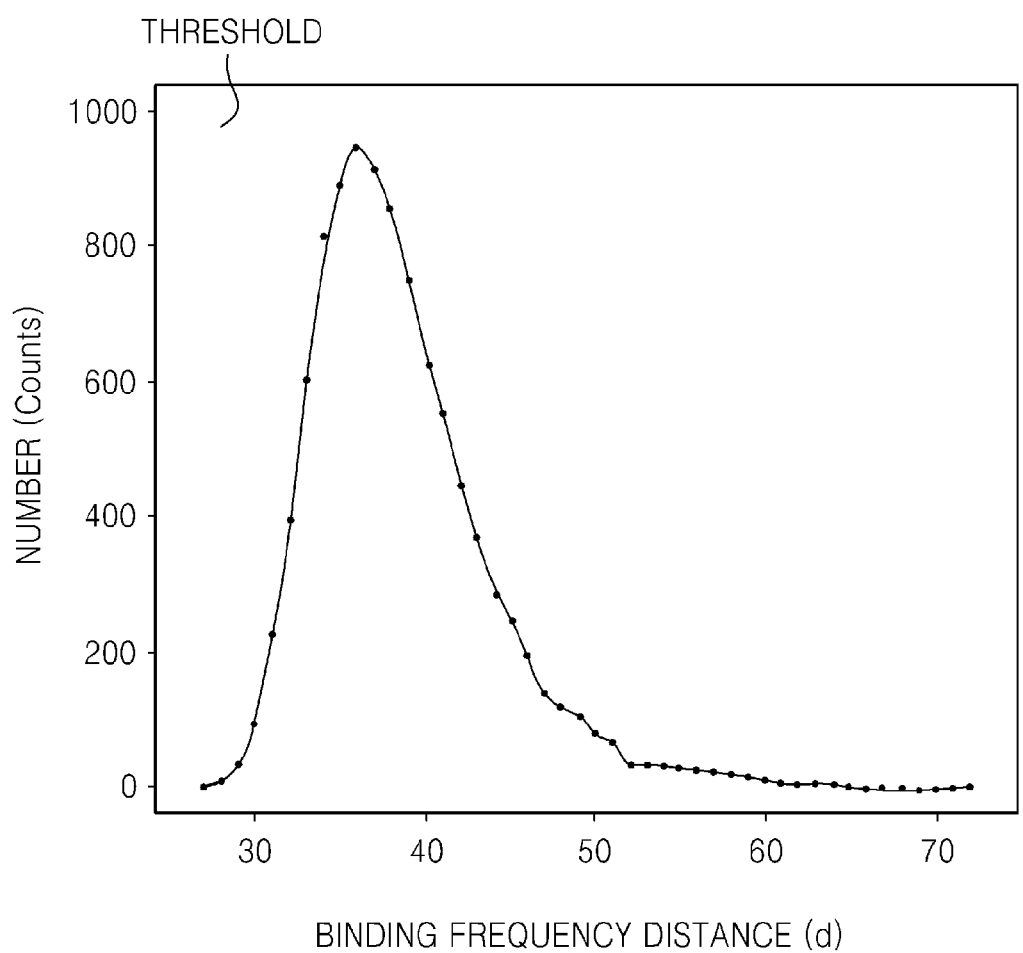
FIG. 5 is a graph of a target-reference distance distribution of binding frequency distance (d) illustrating the number of occurrences (counts) of a binding frequency distance (d) between the target signature of FIG. 1 or FIG. 3 and a reference signature.

FIG. 5 is a target-reference distance distribution of binding frequency distance (d) illustrating the number of counts with respect to the binding frequency distance between the $i^{th}$ binding frequency of the target signature of FIG. 1 or FIG. 3 and the $i^{th}$ binding frequency of a reference signature.

In an embodiment of the target biomolecule identification method, identifying the target biomolecule may further include: calculating a binding frequency distance (d) according to Equation (1) below, wherein N=the number of probe molecules, $x_i$ denotes the $i^{th}$ binding frequency of the target signature, and $y_i$ denotes the $i^{th}$ binding frequency in a reference signature, e.g., a reference signature in a reference signature pool;

$$d(\vec{x}, \vec{y}) = \sqrt{\sum_{i=1}^{N} (x_i - y_i)^2} \qquad \text{Equation 1}$$

generating a target-reference distance distribution of binding frequency distance (d) defined as the number of occurrences (counts) of each binding frequency distance (d); and identifying the target biomolecule as being identical to one of the reference biomolecules having a binding frequency distance (d) from the target biomolecule that is less than or equal to a threshold in the target-reference distance distribution.

The target-reference distance distribution, which is of use for determining whether the target biomolecule having the target signature matches one of the reference signatures of the reference signature pool at a statistical confidence level, is defined as the number of reference molecules in the reference signature pool having a particular binding frequency distance (d) between its reference signature and the target signature.

Methods of generating the target signature and the reference signatures of the reference signature pool are as described above. The term "the $i^{th}$ binding frequency of the target signature" refers to the binding frequency of the $i^{th}$ probe molecule of the N probe molecules with respect to the target biomolecule, and the term "the $i^{th}$ binding frequency of the reference signature" refers to the binding frequency of the $i^{th}$ probe molecule of the N probe molecules with respect the reference biomolecule. The binding frequency of the $i^{th}$ probe molecule of the N probe molecules with respect to the target biomolecule is defined by the $i^{th}$ binding frequency of the target signature, which is denoted by $x_i$, and the binding frequency of the $i^{th}$ probe molecule of the N probe molecules with respect to the reference biomolecule is defined by the $i^{th}$ binding frequency of the reference signature, which is denoted by $y_i$. By inserting the $i^{th}$ binding frequency ($x_i$) of the target signature and the $i^{th}$ binding frequency ($y_i$) of each of the reference signatures of the reference signature pool for each of the N probes into Equation 1 above, a binding frequency distance (d) may be calculated for each of the reference signatures of the reference signature pool. Subsequently, the number of the binding frequency distance (d) relative to the target biomolecule may be counted. In some embodiments, Equation 1 may be replaced with Equation 2 below:

$$d(\vec{x}, \vec{y}) = \frac{\sqrt{\sum_{i=1}^{N} (x_i - y_i)^2}}{N} \qquad \text{Equation 2}$$

In the target-reference distance distribution of FIG. 5, the binding frequency distance (d) is represented on the X-axis, and the number of counts of each binding frequency distance (d) is represented on the Y-axis. A threshold indicating a statistical confidence level may be defined in the target-reference distance distribution, as denoted by the vertical dotted line in FIG. 5. The target biomolecule may be identified as being identical to a reference biomolecule having a binding frequency distance (d) that is less than or equal to the threshold in the target-reference distance distribution. If there are at least two binding frequency distances (d) smaller than or equal to the threshold in the target-reference distance distribution, the target biomolecule may be determined to be identical to one of the reference biomolecules having the smallest binding frequency distance (d). In generating the target-reference distance distribution, generating the target signature may include repeatedly binding each of the N probe molecules to the target biomolecule and calculating an average binding frequency of each of the N probe molecules with respect to the target biomolecule, thereby generating a target signature, which is defined by the average binding frequencies of the individual N probe molecules.

FIG. 7 illustrates a target biomolecule identification method according to another embodiment, which includes repeatedly binding N different probe molecules to a target biomolecule to generate a target signature using average binding frequencies of the N different probe molecules and the standard deviation (S.D.) of each average binding frequency.

In an embodiment of the target biomolecule identification method, generating the target signature may include repeatedly binding each of the N probe molecules to the target biomolecule and calculating an average binding frequency of each of the N probe molecules with respect to the target biomolecule, thereby generating a target signature, which is defined by the average binding frequencies of the individual N probe molecules.

Identifying the target biomolecule may further include: calculating a binding frequency distance (d) according to Equation (3) below, wherein $x_i$ denotes the average binding frequency of the $i^{th}$ probe molecule in the target signature, $y_i$ denotes the binding frequency of the $i^{th}$ probe molecule in a reference signature, e.g., in a reference signature pool, and a denotes the standard deviation of the average binding frequency of the $i^{th}$ probe molecule in the target signature; and $$d(\vec{x}, \vec{y}) = \sqrt{\sum_{i=1}^{n} \frac{(x_i - y_i)^2}{\sigma_i^2}} \quad \text{Equation 3}$$

generating a target-reference distance distribution of binding frequency distance (d) defined as the number of counts with respect to each of the binding frequency distances (d), wherein the target biomolecule may be identified as being identical to one of the reference biomolecules having a binding frequency distance (d) that is less than or equal to a threshold in the target-reference distance distribution.

Methods of generating the target signature and the reference signatures of the reference signature pool are as described above. The target signature is defined by the average binding frequencies of the individual N probe molecules with respect to the target biomolecule, which are obtained by repeatedly binding the N probe molecules to the target biomolecule and calculating the average binding frequency of each of the N probe molecules with respect to the target biomolecule. The term "the average $i^{th}$ binding frequency of the target signature" refers to the average binding frequency of the $i^{th}$ probe molecule of the N probe molecules obtained by repeatedly binding the $i^{th}$ probe molecule to the target biomolecule, and the term "the $i^{th}$ binding frequency of the reference signature" refers to the binding frequency of the $i^{th}$ probe molecule of the N probe molecules with respect to the reference biomolecule. The average binding frequency of the $i^{th}$ probe molecule of the N probe molecules, which is calculated from the result of repeatedly binding molecules of the $i^{th}$ probe to the target biomolecule, is defined by the $i^{th}$ average binding frequency of the target signature, denoted by $x_i$; and the standard deviation of the average binding frequency in the target signature is denoted by $\sigma_i$. The binding frequency of the $i^{th}$ probe molecule of the N probe molecules with respect to the reference biomolecule is defined by the $i^{th}$ binding frequency of the reference signature, which is denoted by y. In the embodiment illustrated in FIG. 7, each of the N probe molecules may be repeatedly bound to the target biomolecule to calculate the average binding frequency of each of the N probe molecules and the standard deviation of each average binding frequency. In particular, referring to FIG. 7, a first probe molecule (AAAAAA) may be repeatedly bound to a target molecule, and subsequently the average binding frequency of the first probe molecule and the standard deviation may be calculated. The same processes may be performed sequentially with a second probe molecule (AAAAAC), a third probe molecule (AAAAAG), a fourth probe molecule (AAAAAT), a fifth probe molecule (AAAATA), and an $N^{th}$ probe molecule (TTTTTT). In the embodiment of FIG. 7, the average binding frequency ($x_i$) and standard deviation ($\sigma_1$) of the first probe molecule were 5 and 1.2, respectively; the average binding frequency ($x_2$) and standard deviation ($\sigma_2$) of the second probe molecule were 6 and 1.4, respectively; the average binding frequency ($x_3$) and standard deviation ($\sigma_3$) of the third probe molecule were 8 and 1.1, respectively; the average binding frequency ($x_4$) and standard deviation ($\sigma_n$) of the fourth probe molecule were 3 and 0.7, respectively; the average binding frequency ($x_5$) and standard deviation ($\sigma_5$) of the fifth probe molecule were 7 and 0.9, respectively; and the average binding frequency ($x_N$) and standard deviation ($\sigma_N$) of the Nth probe molecule were 4 and 0.7, respectively. By inserting the $i^{th}$ binding frequency ($x_i$) of the target signature and the $i^{th}$ binding frequency ($y_i$) of a reference signature of the reference signature pool into Equation 3 above, a binding frequency distance (d) may be calculated for each of the reference signatures of the reference signature pool. The number of reference molecules having a given binding frequency distance (d) may be counted. In this embodiment, Equation 3 may be replaced with Equation 4 below:

$$d(\vec{x}, \vec{y}) = \frac{\sqrt{\sum_{i=1}^{N} \frac{(x_i - y_i)^2}{\sigma_i^2}}}{N} \quad \text{Equation 4}$$

In a target-reference distance distribution of binding frequency distance (d) obtained using Equation 3 or 4, the binding frequency distance (d) is represented on the X-axis, the number of counts with respect to each binding frequency distance (d) may be represented on the Y-axis, and a threshold binding frequency distance indicating a desired statistical confidence level may be determined for the distribution. In this case, the target biomolecule may be identified as being identical to the reference biomolecule having a binding frequency distance (d) that is less than or equal to the threshold in the target-reference distance distribution. If there are at least two binding frequency distances (d) that are less than or equal to the threshold in the target-reference distance distribution, the target biomolecule may be determined to be identical to any one of the reference biomolecules having the smallest binding frequency distance (d).

Figure 8A:
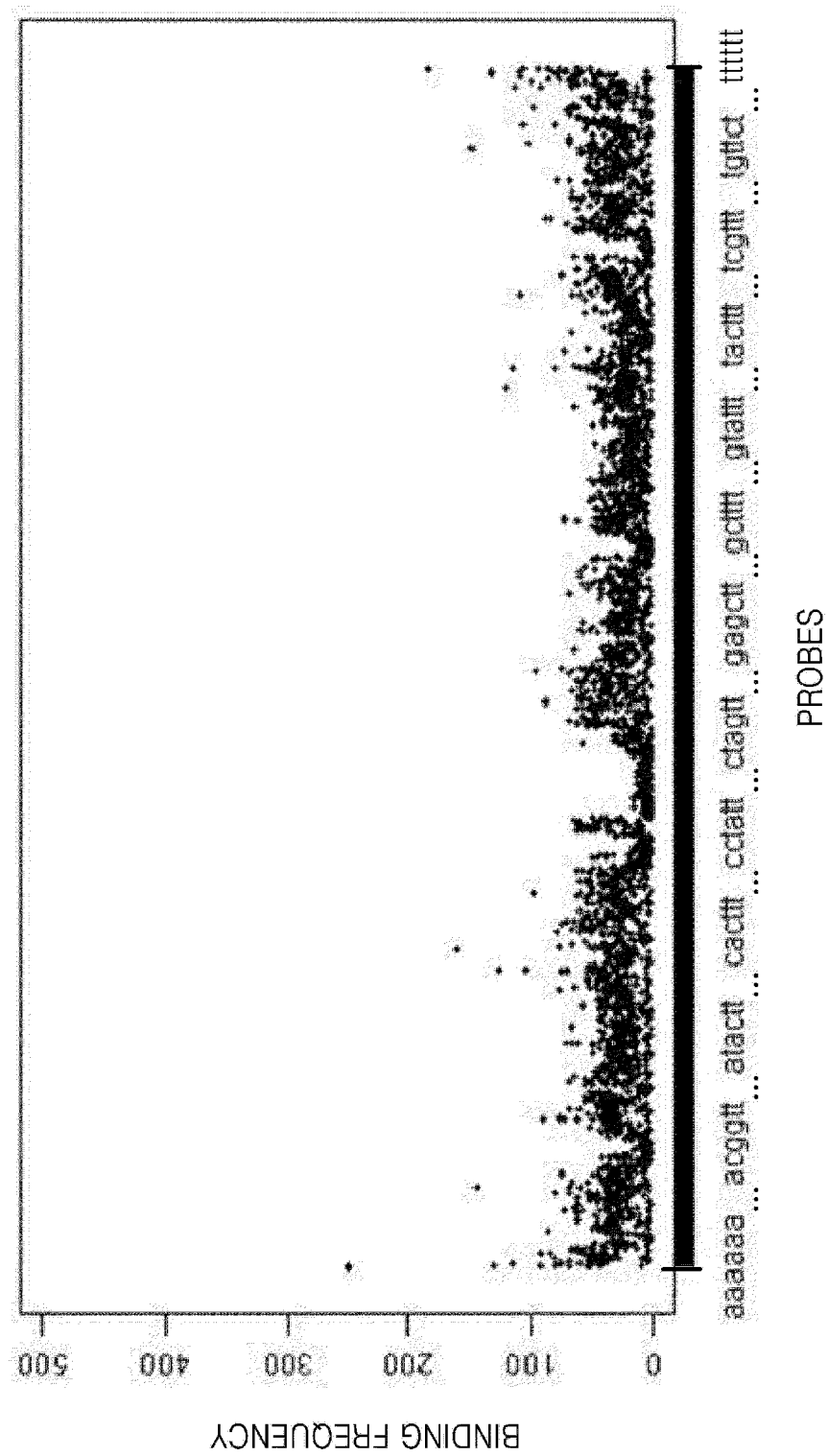
FIG. 8A illustrates a target signature.
Figure 8B:
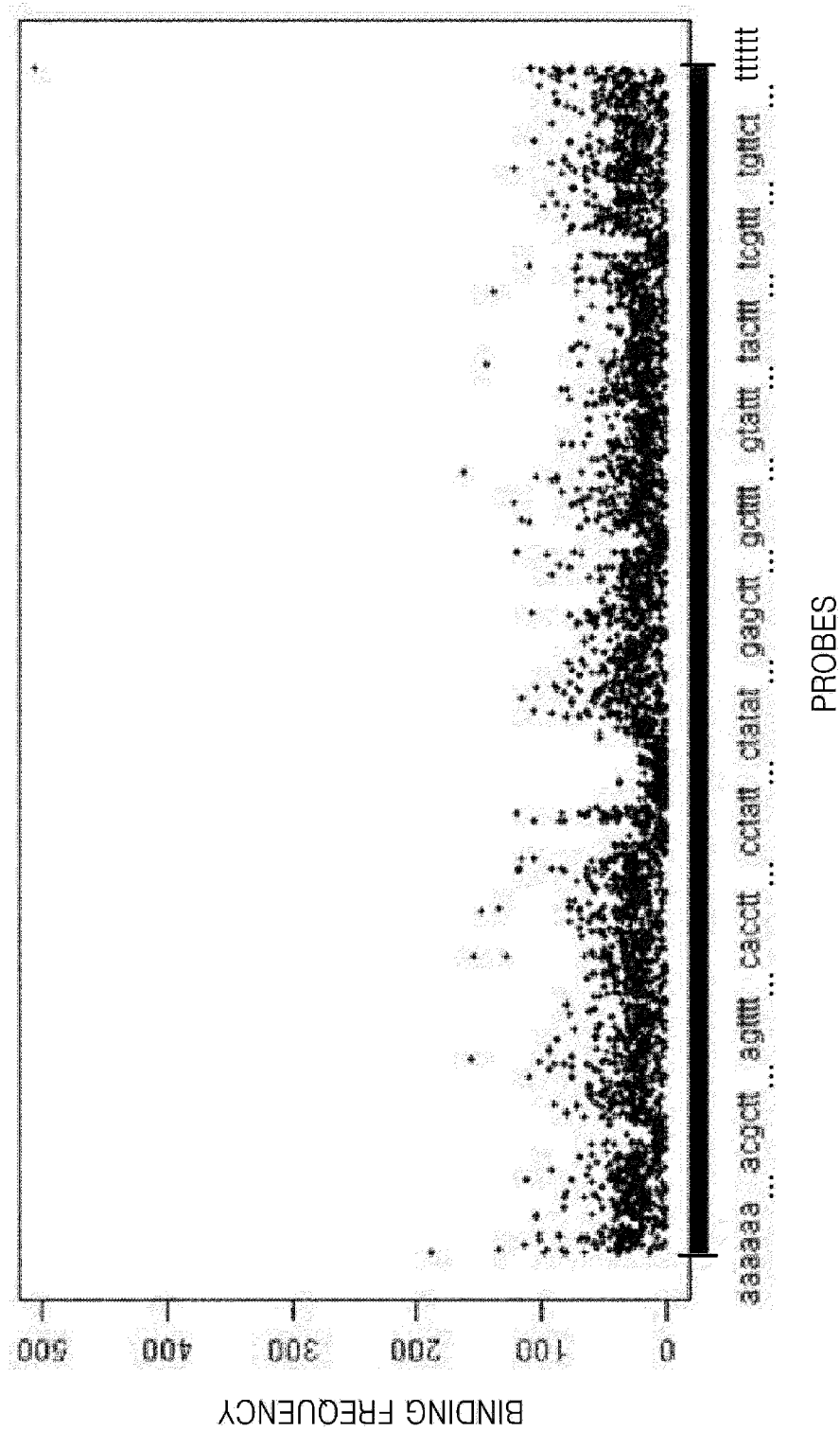
FIGS. 8B and 8C illustrate two reference signatures of a reference signature pool, according to an experimental example.
Figure 8C:
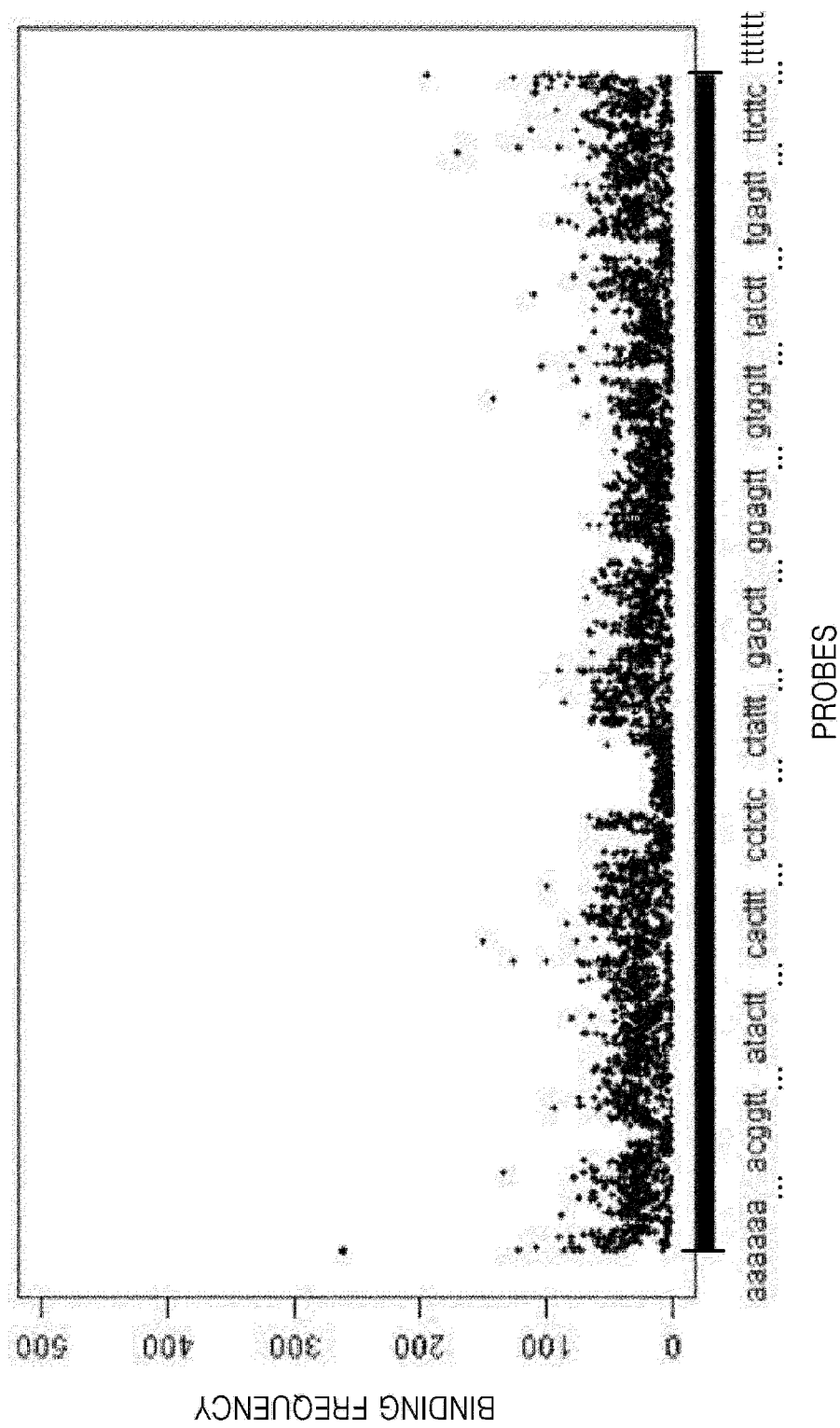

FIG. 8A illustrates a target signature, and FIGS. 8B and 8C illustrate reference signatures of a reference signature pool, according to an experimental example. The target signature in FIG. 8A is of a target nucleic acid, and the reference signatures in FIGS. 8B and 8C are of reference nucleic acids that are a similar kind as the target nucleic acid, but have different base sequences.

To confirm whether the target biomolecules may be accurately identified using the above-described method, the following experiment was conducted. The epidermal growth factor receptor (EGFR, Homo sapiens) gene present on chromosome 7 (55054219-55154219, 100 kb) of humans was selected as a target biomolecule. One hundred arbitrary genes were selected as reference biomolecules. Included among these 100 reference genes were the human EGFR gene ("first reference biomolecule"), a gene present on chromosome 7 of a chimpanzee having the most similar base sequence to the human EGFR gene ("second reference biomolecule"), and a gene present on chromosome 3 of humans having the most similar base sequence within the human genome to the human EGFR gene ("third reference biomolecule"). To generate the target signature of FIG. 8A, a single-stranded nucleic acid molecule of the EGFR gene, and probe molecules having different nucleotide base sequences (aaaaaa, aaaaac, aaaaag, aaaaat, . . . , and tttttt) were prepared. The target signature was generated according to the method illustrated in FIG. 6. To generate reference signatures, base sequences of the selected 100 reference biomolecules were acquired, and the reference signatures of each of the 100 reference biomolecules were generated according to the same method, to form a reference signature pool. The reference signatures shown in FIGS. 8B and 8C are for the chimpanzee gene (the second reference biomolecule) and the human gene on chromosome 3 (the third reference biomolecule), respectively, that have the most similar, but nonidentical, base sequences to that of the EGFR gene (The other ninety eight reference signatures are not illustrated).

Figure 9B:
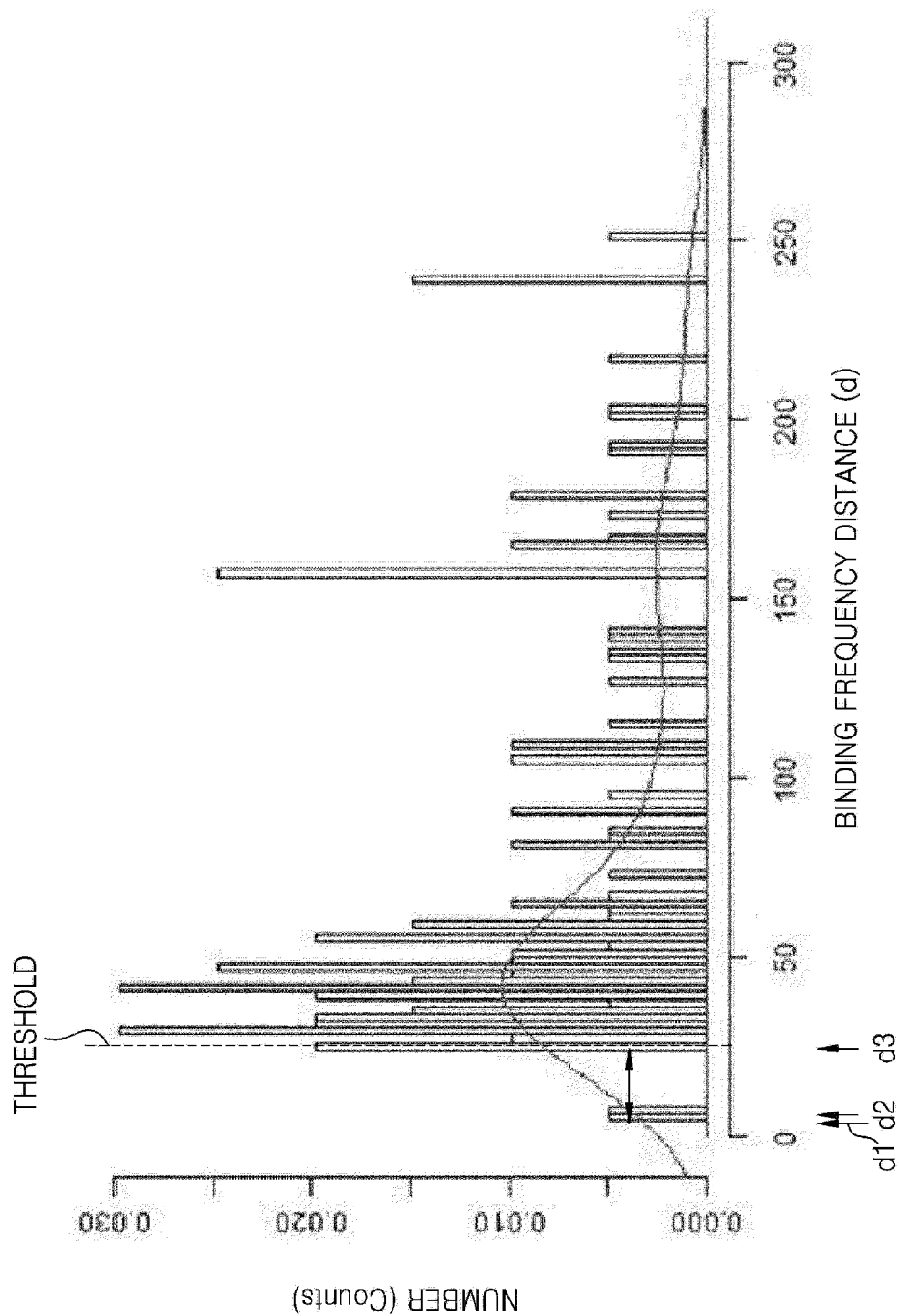

FIGS. 9A to 9C illustrate a method of identifying a target biomolecule with reference to a target-reference distance distribution of binding frequency distance (d), according to the experimental example, in which the location error of the measuring equipment is considered in generating the target-reference distance distribution.

Technical limitations of the measuring equipment used to detect probe-biomolecule binding may result in inaccurate determinations of the binding frequency of a probe, resulting in inaccurate identification results. For example, measuring equipment which detects an optical or electric signal within a predetermined detection resolution may detect one signal generated from a target molecule-probe binding event. However, if two molecules of a probe are bound to the target biomolecule, i.e., a probe having a binding frequency of 2, the measuring equipment may still detect just one signal from both binding events. Such a mechanical error is inherent in the measuring equipment, and thus may cause an unexpected, wrong identification result. For this reason, it was tested whether a target biomolecule may be accurately identified using the method disclosed herein, even if the measuring equipment, e.g., that of the nanopore method illustrated in FIG. 6, causes a location error.

For measuring equipment for detecting the target molecule-probe binding having a resolution of 100 nucleotides, a possible location error of 0 nucleotides, +10 nucleotides, or +50 nucleotides, was set in consideration of the length of the probes (6 nucleotides). The probes were bound to the EGFR gene, and the binding frequencies of the probes were measured, taking the three possible location errors into account. Three target signatures were generated from these three sets of binding frequencies of the probes to the target biomolecule, each of which was then used along with the reference signature pool generated as described with reference to FIGS. 8A to 8C, according to the method described above, to generate a target-reference distance distribution of binding frequency distance (d). FIGS. 9A to 9C illustrate the target-reference distance distributions determined at a location error of 0 nucleotides, +10 nucleotides, and +50 nucleotides, respectively.

According to the results of analyzing the target-reference distance distribution of FIG. 9A, for binding frequencies determined with a location error of 0 nucleotides, the binding frequency distance d1 calculated for the target signature and the reference signature of the first reference biomolecule was 0.31, the binding frequency distance d2 calculated for the target signature and the reference signature of the second reference biomolecule was 78.31, and the binding frequency distance d3 calculated for the target signature and the reference signature of the third reference biomolecule was 762.54. The binding frequency distance d1 in FIG. 9A is a minimum level below a threshold of the target-reference distance distribution, and thus the target nucleic acid molecule may be determined or identified to be the EGFR gene, the first reference biomolecule. Referring to the target-reference distance distribution of FIG. 9B, for binding frequencies determined with a location error of +10 nucleotides, the binding frequency distance d1 calculated for the target signature and the reference signature of the first reference biomolecule was 5.12, the binding frequency distance d2 calculated for the target signature and the reference signature of the second reference biomolecule was 6.68, and the binding frequency distance d3 calculated for the target signature and the reference signature of the third reference biomolecule was 24.41. The binding frequency distance d1 in FIG. 9B is a minimum level below a threshold of the target-reference distance distribution, and thus the target nucleic acid molecule may be determined or identified to be the EGFR gene, the first reference biomolecule. Referring to the target-reference distance distribution of FIG. 9C, for binding frequencies determined with a location error of +50 nucleotides, the binding frequency distance d1 calculated for the target signature and the reference signature of the first reference biomolecule was 6.71, the binding frequency distance d2 calculated for the target signature and the reference signature of the second reference biomolecule was 7.85, and the binding frequency distance d3 calculated for the target signature and the reference signature of the third reference biomolecule was 27.46. The binding frequency distance d1 in FIG. 9C is a minimum level below a threshold of the target-reference distance distribution, and thus the target nucleic acid molecule may be determined or identified to be the EGFR gene, the first reference biomolecule. Therefore, as described with reference to FIGS. 9A to 9C, regardless of the location error of the measuring equipment in determining binding frequencies, the target biomolecule may be accurately identified using the target biomolecule identification method according to embodiments of the present disclosure.

Figure 10A:
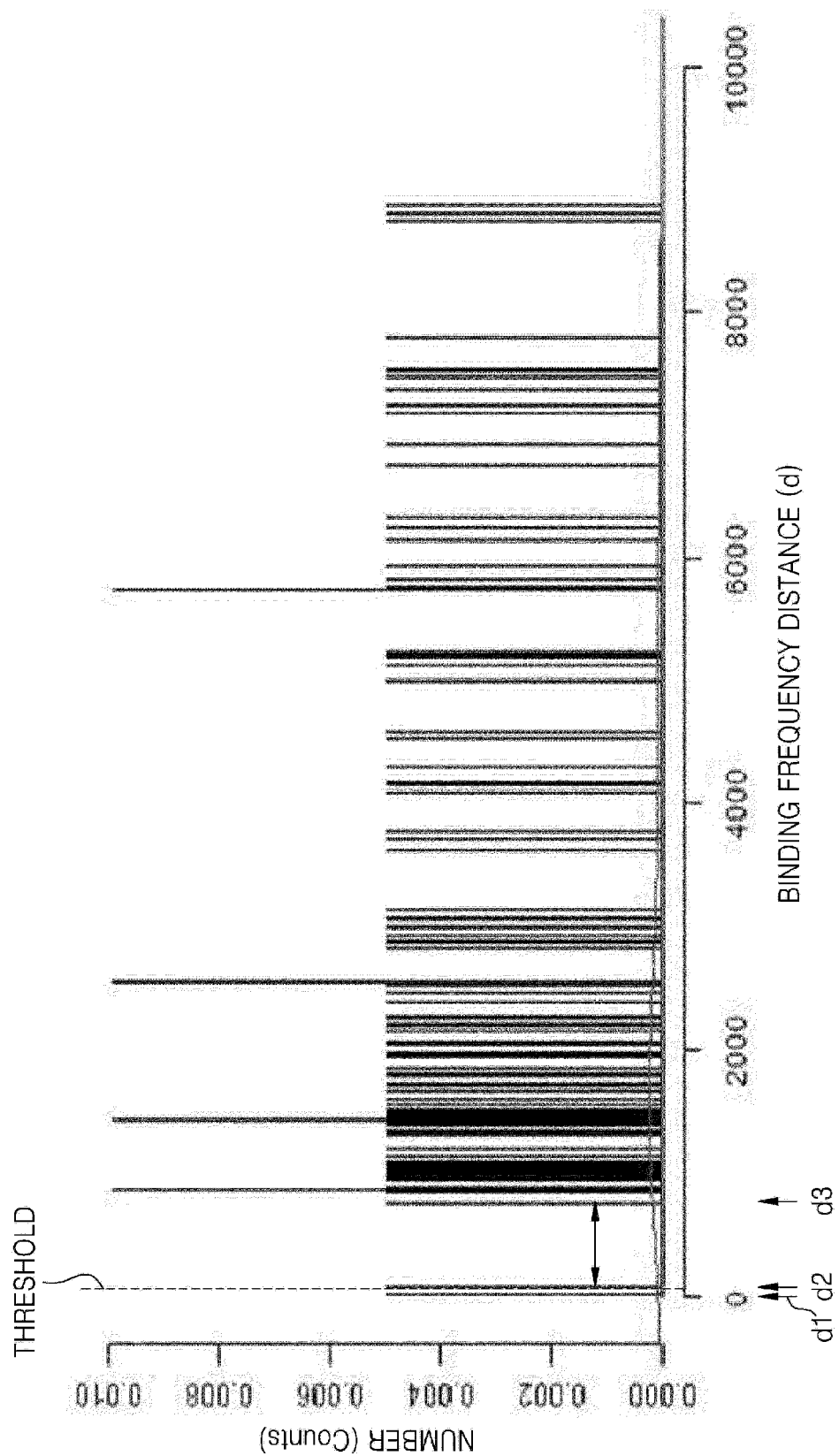
FIGS. 10A, 10B, and 10C each present a target-reference distance distribution of binding frequency distance (d) for a target biomolecule that is a genetic variant of the wildtype target biomolecule determined assuming a possible location error of 0 nucleotides (FIG. 10A), +10 nucleotides (FIG. 10B), or +50 nucleotides (FIG. 10C) for determining binding frequencies with the measuring equipment n.
Figure 10B:
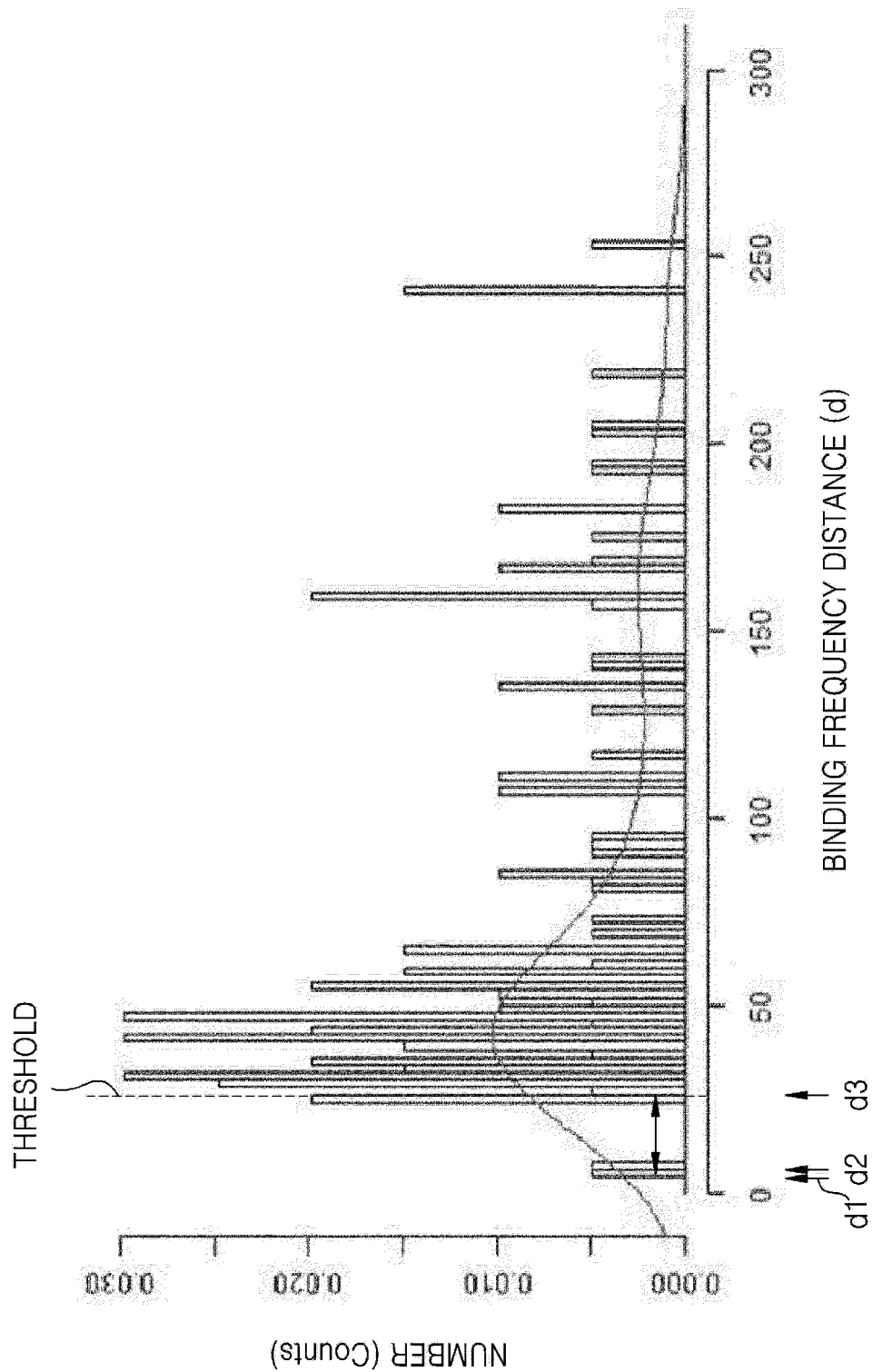
Figure 10C:
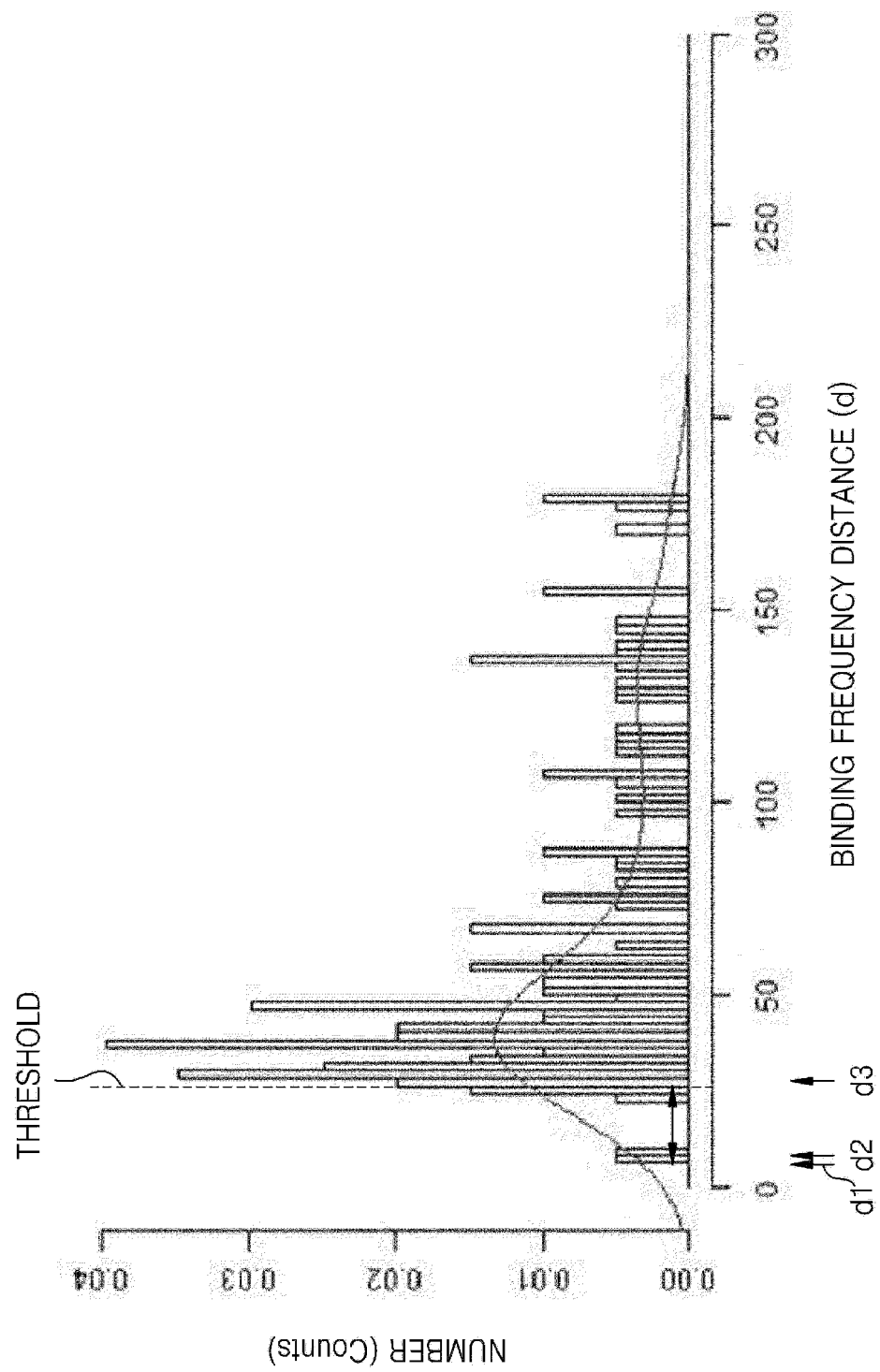

FIGS. 10A to 10C illustrate a method of identifying a target biomolecule with reference to a target-reference distance distribution of binding frequency distance (d), according to another experimental example of the present disclosure, in which the measurement error of the measuring equipment and genetic variations in the target biomolecule are considered in generating the target-reference distance distribution.

In addition to the inherent location error of the measuring equipment, as described in relation to the embodiment of FIG. 9, variations in the target biomolecule itself may cause inaccurate identification results. For example, if a target nucleic acid molecule has a deletion in a region of the wild-type base sequence, the base sequence of the deletion region may be difficult to read, and thus the target nucleic acid molecule may be inaccurately identified. For this reason, it was tested whether a target biomolecule may be accurately identified using the method according to the embodiments of the present disclosure, even if the target biomolecule has a mutation in its subunits and the measuring equipment causes a location error.

The EGFR gene (100 kb) was treated with a specific restriction enzyme to result in a deletion of about 500 bp (about 0.5% of the total length) in a specific base sequence region. The probes were bound to the EGFR gene with the deletion of about 500 bp, and binding frequencies of the probes were measured with measuring equipment having a resolution of 100 bp for detecting target molecule-probe binding and an assumed location error of 0 bp, +10 bp, or +50 bp, which are possible at the set resolution in view of the length of the probes (6 nucleotides). A target signature was generated for each probe for each assumed location error from the binding frequencies of the probes to the target biomolecule, and then used along with the reference signature pool generated as described with reference to FIGS. 8A-to 8C, according to the method described above, to generate a target-reference distance distribution of binding frequency distance (d) for each assumed location error. FIGS. 10A to 10C illustrate the target-reference distance distributions at a location error of 0 bp, +10 bp, and +50 bp, respectively.

According to the results of analyzing the target-reference distance distribution of FIG. 10A, for binding frequencies determined with a location error of 0 bp, the binding frequency distance d1 calculated for the target signature and the reference signature of the first reference biomolecule was 2.1, the binding frequency distance d2 calculated for the target signature and the reference signature of the second reference biomolecule was 79.59, and the binding frequency distance d3 calculated for the target signature and the reference signature of the third reference biomolecule was 758.16. The binding frequency distance d1 in FIG. 10A is a minimum level below a threshold of the target-reference distance distribution, and thus the target nucleic acid molecule may be determined or identified to be the EGFR gene, the first reference biomolecule. Referring to the target-reference distance distribution of FIG. 10B for binding frequencies determined with a location error of +10 bp, the binding frequency distance d1 calculated for the target signature and the reference signature of the first reference biomolecule was 5.40, the binding frequency distance d2 calculated for the target signature and the reference signature of the second reference biomolecule was 6.96, and the binding frequency distance d3 calculated for the target signature and the reference signature of the third reference biomolecule was 24.41. The binding frequency distance d1 in FIG. 10B is a minimum level below a threshold of the target-reference distance distribution, and thus the target nucleic acid molecule may be determined or identified to be the EGFR gene, the first reference biomolecule. Referring to the target-reference distance distribution of FIG. 10C for binding frequencies determined with a location error of +50 bp, the binding frequency distance d1 calculated for the target signature and the reference signature of the first reference biomolecule was 6.92, the binding frequency distance d2 calculated for the target signature and the reference signature of the second reference biomolecule was 8.05, and the binding frequency distance d3 calculated for the target signature and the reference signature of the third reference biomolecule was 23.99. The binding frequency distance d1 in FIG. 10C is a minimum level below a threshold of the target-reference distance distribution, and thus the target nucleic acid molecule may be determined or identified to be the EGFR gene, the first reference biomolecule. Therefore, as described with reference to FIGS. 10A to 9C, regardless of the location error of the measuring equipment and a mutation in the subunits of the target molecule itself, the target biomolecule may be accurately identified using the target biomolecule identification method according to embodiments of the present disclosure.

As described above, according to one or more of the above embodiments of the present disclosure, by using the binding frequencies of a panel of different probes with respect to a target biomolecule, the target biomolecule in a sample may be efficiently and accurately identified.

The terminology used herein is for the purpose of describing particular embodiments only and is not intended to be limiting of the invention. The terms "a" and "an" do not denote a limitation of quantity, but rather denote the presence of at least one of the referenced item. The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A method of identifying a target biomolecule, the method comprising:

detecting the binding of each of N nucleic acid probe molecules to a target biomolecule to generate a target signature, which is defined by the binding frequencies of the individual N nucleic acid probe molecules to the target biomolecule, wherein N≥2 and each nucleic acid probe molecule has a unique configuration element that permits specific binding of the nucleic acid probe molecule to the target molecule, wherein the target biomolecule is a nucleic acid;

comparing the target signature to a reference signature pool, wherein the reference signature pool comprises a reference signature for each of a plurality of reference biomolecules, and each reference signature is defined by the binding frequencies of the individual N nucleic acid probe molecules to a reference biomolecule; and identifying the target biomolecule as being identical to a reference biomolecule if the binding frequencies of the individual nucleic acid probe molecules in the target signature match those in the reference signature within a predetermined confidence level of about 95% or greater with respect to the N nucleic acid probe molecules, wherein identifying the target biomolecule further comprises: calculating a binding frequency distance (d) according to Equation (1) below, wherein $x_i$ denotes an $i^{th}$ binding frequency of the target signature, and $y_i$ denotes an $i^{th}$ binding frequency of each of the reference signatures in the reference signature pool;

$$d(\vec{x}, \vec{y}) = \sqrt{\sum_{i=1}^{N} (x_i - y_i)^2} \quad \text{Equation 1}$$

and generating a target-reference distance distribution of binding frequency distance (d) defined by a number of counts with respect to each of the binding frequency distances (d), wherein the target biomolecule is identified as being identical to one of the reference biomolecules having a binding frequency distance (d) that is smaller or equal to a predetermined threshold in the target-reference distance distribution.

2. The method of claim 1, wherein Equation 1 is replaced with Equation 2 below:

$$d(\vec{x}, \vec{y}) = \frac{\sqrt{\sum_{i=1}^{N}(x_i - y_i)^2}}{N}.$$

Equation 2

3. The method of claim 1, wherein if there are at least two reference biomolecules with reference signatures having binding frequency distances (d) that are smaller than or equal to the threshold in the target-reference distance distribution, the target biomolecule is determined to be identical to the reference biomolecule with the reference signature having the smallest binding frequency distance (d).

4. A method of identifying a target biomolecule, the method comprising:
  detecting the binding of each of N nucleic acid probe molecules to a target biomolecule to generate a target signature, which is defined by the binding frequencies of the individual N nucleic acid probe molecules to the target biomolecule, wherein N≥2 and each nucleic acid probe molecule has a unique configuration element that permits specific binding of the nucleic acid probe molecule to the target molecule, wherein the target biomolecule is a nucleic acid;
  comparing the target signature to a reference signature pool, wherein the reference signature pool comprises a reference signature for each of a plurality of reference biomolecules, and each reference signature is defined by the binding frequencies of the individual N nucleic acid probe molecules to a reference biomolecule; and
  identifying the target biomolecule as being identical to a reference biomolecule if the binding frequencies of the individual nucleic acid probe molecules in the target signature match those in the reference signature within a predetermined confidence level of about 95% or greater with respect to the N nucleic acid probe molecules,
  wherein the generating of the target signature comprises repeatedly binding each of the N nucleic acid probe molecules to the target biomolecule; and calculating an average binding frequency of each of the N nucleic acid probe molecules with respect to the target biomolecule, thereby generating a target signature, which is defined by the average binding frequencies of the individual N nucleic acid probe molecules, and
  the identifying of the target biomolecule further comprises: calculating a binding frequency distance (d) according to Equation (3) below, wherein $x_i$ denotes an $i^{th}$ average binding frequency of the target signature, $y_i$ denotes an $i^{th}$ binding frequency of each of the reference signatures in the reference signature pool, and σi denotes a standard deviation of the $i^{th}$ average binding frequency of the target signature;

$$d(\vec{x}, \vec{y}) = \sqrt{\sum_{i=1}^{N} \frac{(x_i - y_i)^2}{\sigma_i^2}}$$

Equation 3 and generating a target-reference distance distribution of binding frequency distance (d) defined by a number of counts with respect to each of the binding frequency distances (d), wherein the target biomolecule is identified as being identical to one of the reference biomolecules with a binding frequency distance (d) that is smaller or equal to a predetermined threshold in the target-reference distance distribution.

5. The method of claim 4, wherein Equation 3 is replaced with Equation 4 below:

$$d(\vec{x}, \vec{y}) = \frac{\sqrt{\sum_{i=1}^{N} \frac{(x_i - y_i)^2}{\sigma_i^2}}}{N}.$$

Equation 4

6. The method of claim 4, wherein if there are at least two reference biomolecules with reference signatures having binding frequency distances (d) that are smaller than or equal to the threshold in the target-reference distance distribution, the target biomolecule is determined to be identical to the reference biomolecule with the reference signature having the smallest binding frequency distance (d).

* * * * *